Jan. 12, 1954 A. C. STONEMAN Re. 23,774

VACUUM NEUTRALIZATION OF DETERGENTS

Original Filed June 12, 1950 2 Sheets-Sheet 1

INVENTOR.
Alan C. Stoneman,
BY Herbert White
Attorney.

Jan. 12, 1954 A. C. STONEMAN Re. 23,774
VACUUM NEUTRALIZATION OF DETERGENTS
Original Filed June 12, 1950 2 Sheets-Sheet 2
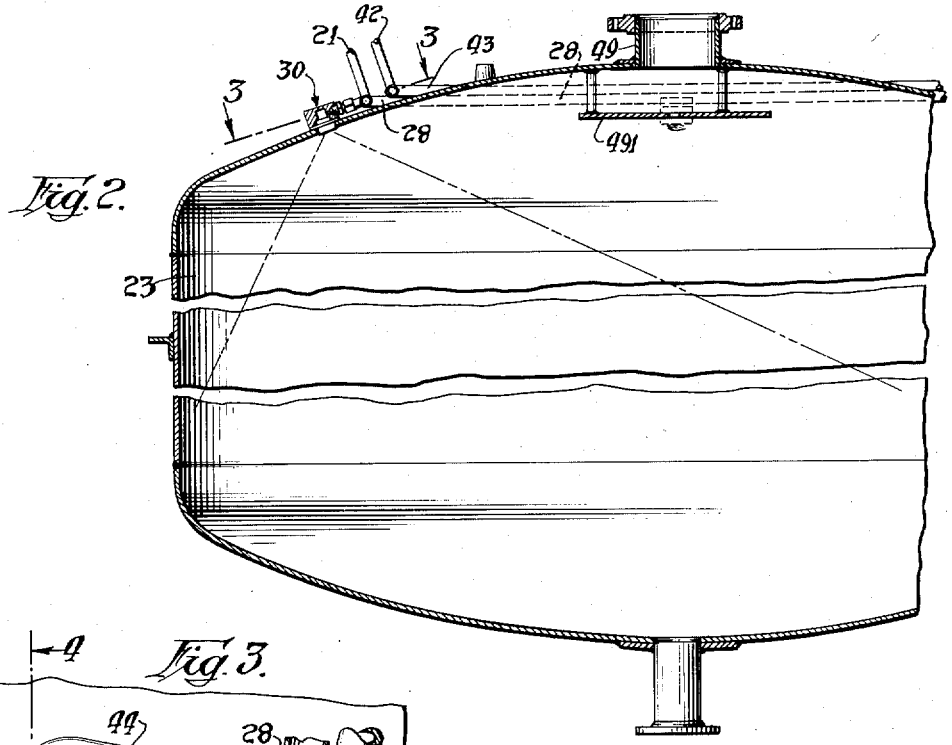
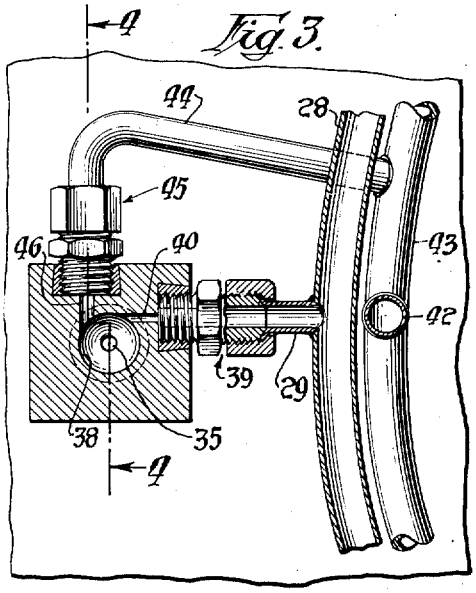
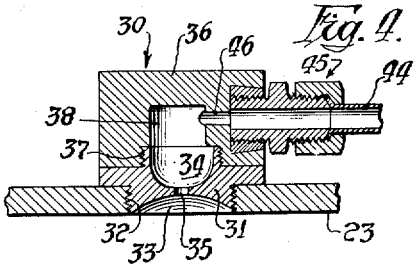
INVENTOR.
Alan C. Stoneman,
BY Harlow White
Attorney.

Reissued Jan. 12, 1954 Re. 23,774

UNITED STATES PATENT OFFICE 23,774

VACUUM NEUTRALIZATION OF DETERGENTS

Alan C. Stoneman, San Marino, Calif., assignor to Purex Corporation, Ltd., South Gate, Calif., a corporation of California Original No. 2,613,218, dated October 7, 1952, Serial No. 167,642, June 12, 1950. Application for reissue July 17, 1953, Serial No. 368,850

13 Claims. (Cl. 252—138)

Matter enclosed in heavy brackets [ ] appears in the original patent but forms no part of this reissue specification; matter printed in italics indicates the additions made by reissue.

This invention relates generally to improved methods for the production of organic compounds suitable for use as detergents, and particularly the alkali metal salts of organic sulfonates and sulfates, which have desirable detergent properties.

In many of its major aspects the invention is concerned primarily with a novel and highly advantageous method for effecting neutralization of a sulfonated or sulfated stock, all in a manner facilitating and benefiting not only the neutralization stage itself, but also resulting in the production of a detergent salt, the properties and condition of which permit further processing, as in a final spray drying stage, to give a superior quality commercial product.

At the outset it may be mentioned that the invention contemplates the use or processing of any suitable organic sulfonates or sulfates, or mixtures thereof, the molecular structures of which following alkali metal neutralization, display detergent properties. Since various classes of such compounds are well known, it will suffice to indicate generally their types and structures. Broadly, such compounds may be regarded as organic sulfates or sulfonates containing an aliphatic or alicyclic part which may or may not be attached to an aromatic ring, with the aliphatic or alicyclic part being derived from compounds containing 8 to 18 carbon atoms and capable of either direct reaction to the sulfates or sulfonates, or indirect reaction by combination with an aromatic ring which in turn is capable of reaction to an organic sulfate or organic sulfonate. Examples of such reactive alkyl radical-containing compounds are found in the 8 to 18 carbon olefins, alcohols, fatty acids, alkyl halides, and esters in the aliphatic or alicyclic series. The sulfonic and sulfuric acid derivatives of these compounds may be designated in the following groups: (1) Organic compounds of the general formula $R—OSO_2—OH$, wherein R is an aliphatic or alicyclic containing 8 to 18 carbon atoms. Examples of this class are n-dodecyl hydrogen sulfate, n-tetradecyl hydrogen sulfate, n-octadecyl hydrogen sulfate, undecane-2-hydrogen sulfate, tridecane-7-hydrogen sulfate, and pentadecane-4-hydrogen sulfate in which the 8 to 18 carbon alkyl radical is derived from the sulfonation of vegetable oil fatty alcohols, or in general mixtures in which the 8 to 18 carbon alkyl radical is derived from aliphatic or alicyclic compounds of either straight or branched, symmetrical or non-symmetrical structure, such as may be found (like the compounds referred to in the following) in distilled petroleum fractions or in other naturally occurring substances. (2) Organic compounds of the general formula $R'—OSO_2—OH$, wherein R′ is any benzoid hydrocarbon radical having two or more nuclear replaceable hydrogen atoms (as derived from benzene, toluene, xylene, phenol) and at least one nuclear hydrogen atom replaced by an aliphatic or alicyclic radical containing 8 to 18 carbon atoms. Examples of this class are dodecane-1-benzene hydrogen sulfate, hexadecane-1-benzene hydrogen sulfate, undecane-1-benzyl hydrogen sulfate, dodecane-2-benzyl hydrogen sulfate, dodecane-2-benzene hydrogen sulfate, or in general mixtures in which the 8 to 18 carbon alkyl radical is derived from aliphatic or alicyclic compounds of either straight or branched, symmetrical or non-symmetrical structure. (3) Organic compounds of the general formula $R''—SO_2—OH$, wherein R″ is an aliphatic or alicyclic radical containing 8 to 18 carbon atoms. Examples of this class are dodecane-1-sulfonic acid, undecane-2-sulfonic acid, hexadecane-8-sulfonic acid, or in general mixtures in which the 8 to 18 carbon alkyl radical is derived from aliphatic or alicyclic compounds of either straight or branched, symmetrical or non-symmetrical structure. (4) Organic compounds of the general formula $R'''—SO_2—OH$, wherein R‴ is any benzenoid hydrocarbon radical having two or more replaceable nuclear hydrogen atoms (as derived from benzene, toluene, xylene), and at least one nuclear hydrogen atom replaced by an aliphatic or alicyclic radical containing 8 to 18 carbon atoms. Examples of this class are the aryl substituted alkanes described in Lewis Patents No. 2,477,382 and No. 2,477,383. Other examples are n-dodecyl benzene sulfonic acid, n-dodecyl toluene sulfonic acid, undecane-2-benzene sulfonic acid, undecane-1-benzyl sulfonic acid, tridecane-2-benzyl sulfonic acid, or in general mixtures in which the 8 to 18 carbon alkyl radical is derived from aliphatic or alicyclic compounds of either straight or branched, symmetrical or non-symmetrical structure.

Since, as indicated, the present invention is concerned primarily with the neutralization stage, and steps beyond, it will be understood that any suitable organic sulfonates or sulfates, or mixtures thereof, included in the designated class and derived or produced in any appropriate manner, may constitute the feed stock for neutralization to alkali metal salts having detergent properties.

With respect now to neutralization, the invention is particularly concerned with the formation of a neutralized product, or slurry, in which the recoverable salt is characterized by its light color and freedom from vaporizable impurities, and the slurry by a controllable consistency and viscosity making it superior for spray drying with additives, to a desirably high density commercial product. It has been found that the temperature of neutralization, reaction rates, admixture of the reactants and simplicity in the overall neutralization operation, are obtainable by conducting the neutralization of an aqueous solution of the reactants under low pressures and temperatures maintained within a range that is found to have a significant relation to the most desirable qualities of the neutralization product.

In accordance with the invention, provision is made for contacting and intimately admixing the acid sulfonated or sulfated hydrocarbon stock with a suitable alkaline neutralizing solution, preferably alkali metal hydroxide solution, under conditions effecting such completeness and intimacy of contact as will promote complete reaction to the point of neutralization and formation of the detergent alkali metal salt. Of critical importance is the maintenance of the reactants under low temperature conditions assuring stabilization of the desired molecular structure of the salt, and at low pressure resulting in the freeing of volatiles from the material, all to the end that the product will be of high quality with respect to color and freedom from excessive contaminants. Of further importance in relation to final drying of a neutralized slurry, if the formation and maintenance of the slurry during neutralization, under low pressure and temperature conditions within particular ranges that have been found to result in desirably high density of the finished product.

The neutralization stage preferably is conducted by first intimately admixing the acid stock and caustic solution in turbulent and high velocity streams within a small mixing zone from which the resulting mixture is sprayed and atomized in finely divided form within an evacuated chamber maintained at a low absolute pressure within the range of about 9 to 88 mm. of mercury and at a corresponding water vapor temperature within a range of about 50° F. to 120° F. It is found that operating within this pressure and temperature range gives to the neutralized salt the desirable light color and purity referred to in the foregoing, and to the resulting slurry a viscosity maintainable within the range of 500 to 1500 centipoises at 100° F., contributing to the desirably high density of the finished product. To assure most efficient distribution and intimacy of contact between the reactants at the point of their admixture, as within a spray nozzle, provision is made for maintaining a continuous recirculation of the slurry into the nozzle, the slurry constituting an alkali carrier as a dispersing and solubilizing medium for promoting fine particle division and reaction of the acidic and alkaline materials.

According to a preferred method of an operation, the neutralization process is started using a measured quantity of caustic solution placed in the vessel or vessels constituting, in effect, the low pressure neutralizing zone, alkali content of the solution being substantially the stoichiometrical equivalent of a measured quantity of the acidic stock to be neutralized. At the start of and throughout neutralization cycle, the acid stock is fed at a measured rate to a stream of the caustic solution being continuously recirculated from an accumulated body in the low pressure zone to the spray nozzle, all in a manner such that as neutralization progresses, the caustic solution acquires increasing quantities of the neutralized salt, and the character of a slurry, while the solution or slurry continuously loses water by reason of the low pressure-induced vaporization. At all times during the neutralization however, the slurry contains reactive alkali at concentrations which are at least sufficient for complete neutralization of the acid stock. Thus, recirculation of the slurry and feeding of the acid stock continue until the entire measured quantity of the latter is taken into the neutralizer.

Thereafter, the neutralized residue may be given any further desired disposition or treatment. Preferably, I control the naturalization to produce a final slurry having a viscosity within the indicated range, which then may be spray dried, ordinarily following addition to the slurry of suitable builders or fillers. While as previously explained, the slurry is advantageously preconditioned by the present methods to promote formation of a desirably high density spray-dried product, it is found that the quality of the product in this respect may be further improved by subjecting the slurry, and following incorporation therein of any additives, to a final deaeration at sufficiently low pressure to effect the removal of air and volatiles present in the mixture. This final deaeration of the slurry is more particularly dealt with in Patent No. 2,606,156 entitled "Deaeration and Drying of Water-Soluble Sulfonated Detergent Compositions," issued August 5, 1952.

All the various features and objects of the invention, as well as the details of certain typical and illustrative procedures, will be explained to best advantage in the following description of the accompanying drawings, in which:

Fig. 2 is a fragmentary sectional view of the neutralizer chamber;

Fig. 3 is an enlarged fragmentary section on line 3—3 of Fig. 2; and

Fig. 4 is a cross-section on line 4—4 of Fig. 3.

Figure 1:
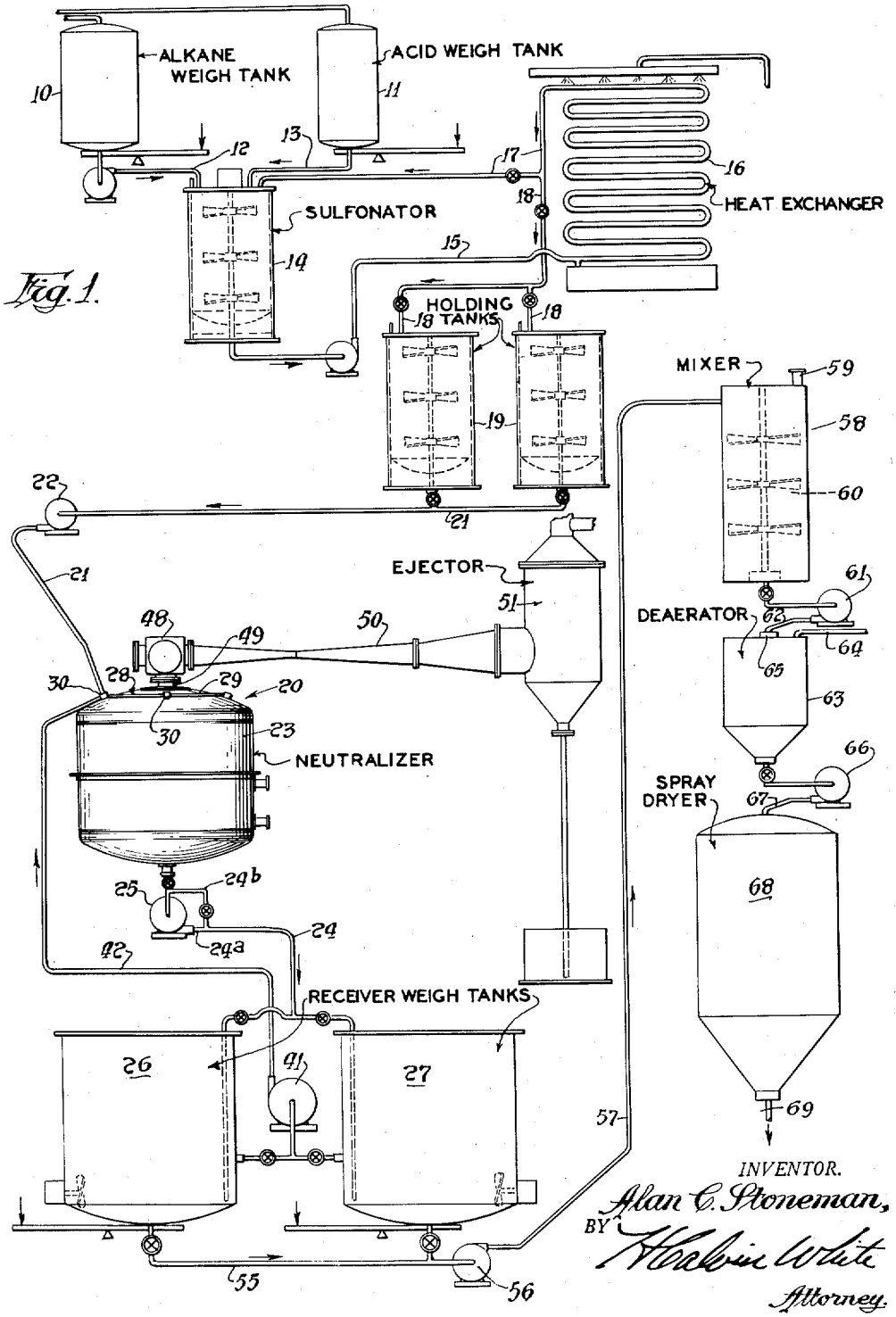
Fig. 1 is a flow sheet illustration of the process.

Merely as illustrative of the derivation of the acidic hydrocarbon stock to be treated, Fig. 1 shows a preliminary sulfonation stage employing weighing tanks 10 and 11, the former containing any suitable alkane, i. e., sulfonatable or sulfatable hydrocarbon, or hydrocarbon mixtures, typically a mixture of benzenoid hydrocarbons having two or more hydrocarbon atoms, replaceable by sulfonation, the benzenoid radical having an attached alkyl group containing 8 to 13 carbon atoms. Tank 11 may contain 25% solution of oleum. From the weight tanks, the alkane and acid are fed through lines 12 and 13 to the sulfonator 14 wherein the materials are subjected to suitable mixing and mechanical agitation. From the sulfonator the mixture is pumped through line 15 and the water cooled heat exchanger 16 to be recirculated back into the sulfonator through line 17. When the sulfonation is complete, the material is pumped through lines 18 into one or the other of the holding tanks 19. The latter thus will be understood to contain a predetermined quantity of the sulfonate of known total acidity. Delivery of the sulfonate from one or the other of tanks 19 to the neutralizer, generally indicated at 20, occurs through line 21 containing the pump 22.

The neutralizing equipment in its entirety is regarded as including a closed chamber 23 communicating through line 24 with one or the other of the closed receiver weigh tanks 26 and 27, the latter being located below chamber 23 a distance at least as great as the height of a barometric water leg, and for example about 40 feet. With chamber 23 evacuated in the manner already explained, and in communication with tanks 26 or 27 through line 24, the neutralizer chamber and the weigh tank in communication therewith during a neutralizing operation, may together be regarded as constituting the entire neutralizing zone, and chamber 20 the low pressure part of the neutralizing zone. The solution or slurry in the chamber 23 may discharge downwardly by gravity through line 24 into the weigh tank, in which event line 24 may take the form of a straight vertical barometric leg. Or for such purposes as to economize in the structural or building height required to accommodate the neutralizer equipment in a vertical distance less than the height of a barometric leg, I may discharge the slurry from the neutralizer down into the weigh tank by one or a series of pumps 25 in branch 24a of line 24, with branch 24b closed or eliminated. As will be understood, the displacement capacity of the pump or pumps will be sufficient for maintenance of the specified pressure conditions in chamber 23.

The sulfonated stock is delivered from line 21 into an annular header 28 at the top of the neutralizing chamber 23 and from which the stock is fed through branches 29 to spray heads or nozzles (typically four), generally indicated at 30, mounted in circularly spaced arrangement in the head of the chamber. Referring to Fig. 4, each spray head comprises a nozzle 31 threaded into an opening 32 in the chamber shell and having an inside concave face 33 to which fluid is discharged from an upper concavity 34 in the nozzle, through opening 35. Each spray head has a body 36 threaded at 37 on the nozzle and containing a mixing chamber 38 in axial alinement with the nozzle. The sulfonate is discharged from header 28 through fitting 39 and passage 40 tangentially into the chamber 38.

As will appear, continuously during the neutralization, a quantity of the solution or slurry contained in one or the other of tanks 26 and 27 in use at the time is recirculated to the spray heads 30 by pump 41 through line 42 connecting with header 43. From the header, the slurry is discharged through branches 44, fitting 45 and passage 46 leading tangentially into the mixing chamber 38, at 90 degrees from the sulfonate inlet passage 40. The two streams thus being discharged through the restricted passages 40 and 46 tangentially and in the same direction within chamber 38 undergo turbulent and thorough mixing, with intimacy of contact between the reactants being promoted by reason of the solubilizing and dispersing functions of those components of the recirculated stream in addition to the caustic. Since the rate of delivery of the recirculated stream to the mixing chamber 38 is desirably in volume excess over the rate of sulfonate delivery thereto, passage 46 may be made somewhat larger than the bore 40.

Chamber 23 and the communicating receiver 26 or 27, are evacuated as by way of a head 48 connected to the shell vapor outlet 49 and communicating through duct 50 with the conventionally illustrated steam ejector 51. As previously indicated, the absolute pressure within chamber 23 and the communicating weigh tank is maintained within a range of 9 to 88 mm. of mercury, at which pressure the temperature of the slurry becomes established in accordance with the cooling effect of the water vaporization within the range of about 50° F. to 120° F. By reason of the low pressure in the neutralizer and the form of the nozzles 31, the recirculated slurry components are discharged in finely atomized spray patterns within chamber 23, and the resultant slurry is taken on down through line 24 into the weigh tank. Water vapor formed in the low pressure chamber is drawn off to the ejector through outlet 49, below which is mounted a baffle 49l to prevent spray loss.

At this point it may be mentioned that preparatory to the neutralizing circulation, a weighed quantity of solution containing caustic soda in a quantity substantially stoichiometrically equivalent to the sulfonate, is contained in one of the tanks 26 or 27. At the start of neutralization, the recirculated stream is caustic soda solution, and as neutralization continues with formation of the sodium sulfonate salts, the caustic solution becomes progressively a slurry of increasing salt concentration, until finally at the point of neutralization of all the sulfonate charge, substantially all the caustic may have become consumed. At this stage of complete neutralization, the slurry and tank 26 or 27 is brought within a viscosity range of from 500 to 1500 centipoises at 100° F.

The following is a tabulation of data in a typical run:

Table I

| | |
|---|---|
| Alkane in tank 10 | 10,000 lbs. |
| 25% Oleum in tank 11 | 10,775 lbs. |
| 25.40 Baumé caustic soda solution (19.5%) in receiver 26 or 27. | 39,230 lbs. |
| Acid addition time to sulfonator | 14 hrs. 35 min. |
| Maximum temperature during acid addition to sulfonator. | 93° F. |
| Maximum temperature during digestion in sulfonator. | 94° F. |
| Time of sulfonic acid delivery to neutralizer. | 12 hrs. 25 min. |
| Total potential amount of water available. | 35,000 lbs. |
| Total water removed by evaporation | 4,400 lbs. |
| Average flow rate of sulfonic acid to neutralizer. | 2.5 gal. per min. |
| Approximate recirculation rate of caustic and slurry. | 40 to 80 gal. per min. |
| Neutralizer chamber temperature | 90° F. to 120° F. |
| Vacuum chamber absolute pressure | 12 to 31 mm. mercury. |

The slurry produced was found to have approximately the following analysis:

Table II

| | | |
|---|---|---|
| Active detergent content | per cent | 27.3 |
| Salt cake ($Na_2SO_4$) | do | 21.2 |
| Unreacted stock | do | 0.3 |
| pH of slurry | | 8.3 |
| Reflectance color | | 73 |
| Viscosity at 100° F. | c. p. | 900 |

Considering now further treatment of the slurry, following completion of the neutralization cycle, the slurry is taken from tank 26 or 27 by way of line 55 and is discharged by pump 56 through line 57 into an appropriate mixer 58, wherein there may be added to the slurry any suitable builder or builders (such as soda ash, sodium bicarbonate, alkali metal silicate, borax, alkali metal phosphate, sodium citrate or sodium carboxy methyl cellulose), together with any of the usual fillers (such as sodium sulfate, sodium chloride, fuller's earth or silica). As illustrative, the mixer 38 is shown to have an additive inlet 59 and to contain a suitable agitator 60. During the mixing, air is introduced to and retained by the mixture in quantities tending to lower the density of the final spray dried product below the higher density desired for the active concentration of the product.

This condition is cured by discharging the mixture by pump 61 through line 62 into a deaerator 63 comprising an enlarged chamber evacuated through line 64 to maintain within the chamber an absolute pressure within the range of about from 50 to 250 mm. of mercury. The mixture is discharged into the chamber through an appropriate spray head 65 so that the materials become finely dispersed and therefore efficiently deaerated in the low pressure atmosphere. From the deaerator, the slurry is discharged by pump 66 through line 67 into a spray drier 68, for example of the type shown in my Patent No. 2,555,516 on "Spray Drier," issued June 5, 1951. In the drier the slurry is air-dispersed and dehydrated to form a finished granular product continuously discharged at 69 from the bottom of the drier.

I claim:

1. The method of neutralizing an acidic stock of the class consisting of sulfonated and sulfated organic compounds having an aliphatic radical containing between about 8 to 18 carbon atoms and the alkali metal salts of which have detergent properties, that includes converting said stock to a slurry of a water dispersable alkali metal salt thereof by [discharging a mixture] *introducing separated streams* of said stock and an aqueous solution of an alkali metal hydroxide *into a plurality of small chambers wherein the streams are intimately admixed while flowing at high velocity, then spraying the mixed materials* in finely divided form openly and through an extended path within the atmosphere of a zone maintained at an absolute pressure between about 9 to 88 mm. of mercury and at a temperature between about 50° F. to 120° F., limiting dehydration of the mixture to produce a flowable slurry, and flowing the slurry from said zone.

2. The method of neutralizing an acidic stock of the class consisting of sulfonated and sulfated organic compounds having an aliphatic radical containing between about 8 to 18 carbon atoms and the alkali metal salts of which have detergent properties, that includes converting at an absolute pressure between about 9 to 88 mm. of mercury and at a temperature between about 50° F. to 120° F. said stock in an aqueous mixture to a water dispersable alkali metal salt thereof contained in a flowable slurry by [discharging a mixture] *introducing separated streams* of said stock and an aqueous solution of an alkali metal hydroxide *into a plurality of small chambers wherein the streams are intimately admixed while flowing at high velocity, then spraying the mixed materials* in finely divided form openly through an extended path within the atmosphere of a zone maintained under said pressure and free falling from the locus of spraying to a collection body of the slurry in the lower portion of said zone, limiting dehydration of the mixture to produce a flowable slurry, and continuously flowing the slurry from said zone during its formation.

3. The method of neutralizing an acidic stock of the class consisting of sulfonated and sulfated organic compounds having an aliphatic radical containing between about 8 to 18 carbon atoms and the alkali metal salts of which have detergent properties, that includes converting at an absolute pressure between about 9 to 88 mm. of mercury and at a temperature between about 50° F. to 120° F. said stock in an aqueous mixture to a water dispersable alkali metal salt thereof contained in a flowable slurry having at 100° F. a viscosity between about 500 to 1500 centipoises by [discharging a mixture] *introducing separated streams* of said stock and an aqueous solution of an alkali metal hydroxide *into a plurality of small chambers wherein the streams are intimately admixed while flowing at high velocity, then spraying the mixed materials* in finely divided form openly and through an extended path within the atmosphere [at] *of* a zone maintained under said pressure, limiting dehydration of the mixture to produce a flowable slurry, and continuously flowing the slurry from said zone during its formation.

4. The method of neutralizing an acidic stock of the class consisting of sulfonated and sulfated organic compounds having an aliphatic radical containing between about 8 to 18 carbon atoms and the alkali metal salts of which have detergen properties, that includes [discharging a stream] *introducing separated streams* of said stock together with an aqueous alkali metal hydroxide solution *into a plurality of small chambers wherein the streams are intimately admixed while flowing at high velocity, then spraying the mixed materials* into a zone maintained at a subatmospheric pressure between about 9 to 88 mm. of mercury and at a temperature between about 50° F. to 120° F. wherein the resulting mixture is cooled by water vaporization from the mixture caused by the low pressure in the zone, limiting dehydration of the mixture to produce a flowable slurry, recirculating an aqueous slurry of reacted stock and alkali from said zone into said stream of the stock being discharged into said zone and flowing the product slurry from said zone.

5. The method of neutralizing an acidic stock of the class consisting of sulfonated and sulfated organic compounds having an aliphatic radical containing between 8 to 18 carbon atoms and the alkali metal salts of which have detergent properties, that includes [spraying a stream] *introducing separated streams* of said stock [together with] *and* an aqueous alkali metal hydroxide solution *into a plurality of small chambers wherein the streams are intimately admixed while flowing at high velocity, then spraying the mixed materials* openly and in free falling dispersion within a zone maintained at a subatmospheric pressure wherein the resulting mixture is cooled by water vaporization from the mixture caused by the low pressure in the zone, the mixture being maintained in said zone at an absolute pressure between about 9 to 88 mm. of mercury and at a temperature between about 50° F. to 120° F., repeatedly and continuously recirculating an aqueous slurry of reacted stock and alkali from said zone into said stream of the stock and throughout the period of its sprayed injection into said zone, and continuously depleting the water content of the recirculated slurry by the low pressure induced water vaporization to produce a flowable and pumpable slurry.

6. The method of neutralizing a quantity of an acidic stock of the class consisting of detergent-forming sulfonated and sulfated organic compounds having an aliphatic radical containing between 8 to 18 carbon atoms with an aqueous solution of a substantially stoichiometrical quantity of an alkali metal hydroxide, that includes maintaining said alkali solution in a low pressure zone, continuously evacuating said zone and maintaining therein a pressure between about 9 to 88 mm. of mercury and an essentially water vapor atmosphere having a temperature between about 50° F. to 120° F., continuously injecting [a stream of] *separate streams of said solution and* said stock into a *plurality of* relatively small mixing [zone] *chambers* and then immediately in spray form into said low pressure zone, continuously recirculating said alkali solution together with neutralized acidic compounds from said low pressure zone into said mixing [zone] *chambers* substantially throughout injection of said stock into the [zone] *mixing chambers* so that the alkali solution and neutralized compound are intimately mixed with the stock and immediately sprayed therewith into the low pressure zone and the recirculation is continued until all the acidic stock is neutralized, limiting dehydration of the mixture to produce a flowable slurry, and flowing the slurry from said zone.

7. The method of neutralizing an acidic detergent-forming stock composed predominately of a mixture of benzenoid hydrocarbons in which the benzenoid radical has an attached alkyl group containing between 8 to 18 carbon atoms and has at least one hydrogen atom replaced by an —$OSO_2OH$ radical, that includes converting said stock to a slurry of a water dispersable alkali metal salt thereof by [discharging a mixture] *introducing separated streams* of said stock and an aqueous solution of an alkali metal hydroxide *into a plurality of small chambers wherein the streams are intimately admixed while flowing at high velocity, then spraying the mixed materials* in finely divided form openly and through an extended path within the atmosphere of a zone maintained at an absolute pressure between about 9 to 88 mm. of mercury and at a temperature between about 50° F. to 120° F., limiting dehydration of the mixture to produce a flowable slurry, and flowing the slurry from said zone.

8. The method of neutralizing with a quantity of an alkali metal hydroxide a substantially stoichiometrical quantity of an acidic detergent-forming stock composed predominately of a mixture of benzenoid hydrocarbons in which the benzenoid radical has an attached alkyl group containing between 8 to 18 carbon atoms and has at least on hydrogen atom replaced by an —$OSO_2OH$ radical, that includes maintaining said alkali solution in a lower collecting zone, continuously injecting [a stream] *separate streams* of said stock into a *plurality of* relatively small mixing [zone] *chambers* and then immediately in spray form into an enlarged low pressure neutralizing zone above the collecting zone and from which the sprayed material passes into the collecting zone, continuously recirculating said alkali solution together with neutralized stock from said collecting zone into said mixing [zone] *chambers* substantially throughout spraying of said stock into the zone so that the recirculated alkali and neutralized stock are intimately mixed with and in larger quantity than the stock and immediately sprayed therewith into the low pressure zone, continuously evacuating said neutralizing zone and maintaining the material therein at a pressure between about 9 to 88 mm. of mercury and at a temperature between about 50° F. to 120° F., continuously depleting said slurry of its water content by virtue of the existent pressure to produce a flowable slurry having a viscosity at 100° F. between about 500 to 1500 centipoises, and continuously flowing said slurry from said neutralizing zone downwardly into the collecting zone.

9. The method of producing a detergent product from a base stock of the class consisting of sulfonated and sulfated organic compounds having an aliphatic radical containing between about 8 to 18 carbon atoms and the alkali metal salts of which have detergent properties, that includes converting said stock to an aqueous slurry of a water dispersable alkali metal salt of the stock by discharging a mixture of said stock and an aqueous solution of an alkali metal hydroxide in finely divided form openly and through an extended path within the atmosphere of a zone maintained at an absolute pressure between about 9 to 88 mm. of mercury and at a temperature between about 50° F. to 120° F., limiting dehydration of the mixture to produce a flowable slurry, mixing solid additives with the slurry, deaerating the resulting mixture at subatmospheric pressure, and spray drying the deaerated mixture.

10. The method of producing a detergent product from a base stock of the class consisting of sulfonated and sulfated organic compounds having an aliphatic radical containing between 8 to 18 carbon atoms and the alkali metal salts of which have detergent properties, that includes converting said stock to an aqueous slurry of a water dispersable alkali metal salt of the stock by [spraying a mixture] *introducing separated streams* of said stock and an aqueous solution of an alkali metal hydroxide *into a plurality of small chambers wherein the streams are intimately admixed while flowing at high velocity, then spraying the mixed materials* in finely divided form openly and through an extended path within the atmosphere of a zone maintained at an absolute pressure between about 9 to 88 mm. of mercury and at a temperature between about 50° F. to 120° F., limiting dehydration of the mixture to produce a flowable slurry, mixing solid additives with the slurry, deaerating the resulting mixture at an absolute pressure between about 50 to 250 mm. of mercury, and spray drying the deaerated mixture.

11. The method of neutralizing an acidic stock of the class consisting of sulfonated and sulfated organic compounds having an aliphatic radical containing between about 8 to 18 carbon atoms and the alkali metal salts of which have detergent properties, that includes converting said stock to a slurry of a water dispersable alkali metal salt thereof by [spraying a mixture] *introducing separated streams* of said stock and an aqueous solution of an alkali metal hydroxide *into a plurality of small chambers wherein the streams are intimately admixed while flowing at high velocity, then spraying the mixed materials* in finely divided form openly and through an extended path within the atmosphere of a zone maintained at an absolute pressure between about 9 to 88 mm. of mercury and at a temperature between about 50° F. to 120° F., limiting dehydration of the mixture to produce a flowable slurry, flowing the slurry into a drying zone and therein spray drying the slurry to produce a granular product.

12. The method of neutralizing an acidic detergent-forming stock composed predominately of a mixture of benzenoid hydrocarbons in which the benzenoid radical has an attached alkyl group containing between 8 to 18 carbon atoms and has at least one hydrogen atom replaced by an —$OSO_2OH$ radical, that includes converting said stock to a slurry of a water dispersable alkali metal salt thereof by [discharging a mixture] *introducing separated streams* of said stock and an aqueous solution of an alkali metal hydroxide *into a plurality of small chambers wherein the streams are intimately admixed while flowing at high velocity, then spraying the mixed materials* in finely divided form openly and through an extended path within the atmosphere of a zone maintained at an absolute pressure between about 9 to 88 mm. of mercury and at a temperature between about 50° F. to 120° F., limiting dehydration of the mixture to produce a flowable slurry, mixing a solid additive with the slurry, and spray drying the resulting mixture.

13. The method of neutralizing an acidic stock of the class consisting of sulfonated and sulfated organic compounds having an aliphatic radical containing between about 8 to 18 carbon atoms and the alkali metal salts of which have detergent properties, that includes converting said stock to a slurry of a water dispersable alkali metal salt thereof by [intimately mixing] *introducing separate streams of* the acidic stock and an aqueous alkali metal hydrovide [solution in a turbulent and high velocity stream within a]

*tangentially into each of a plurality of circular and* relatively small mixing [zone] *chambers,* then suddenly discharging the high velocity mixture *axially from the chambers* in finely divided form openly and through an extended path within the atmosphere of an enlarged zone maintained at an absolute pressure between about 9 to 88 mm. of mercury and at a temperature between about 50° F. to 120° F. at which the mixture particles undergo cooling by virtue of water vaporization therefrom induced by the low pressure, limiting dehydration of the mixture in said zone to produce a flowable slurry, and flowing the slurry from said zone.

ALAN C. STONEMAN.

References Cited in the file of this patent or the original patent

UNITED STATES PATENTS

| Number | Name | Date |
|---|---|---|
| 1,968,797 | Bertsch | July 31, 1934 |
| 2,162,269 | Mikeska | June 13, 1939 |
| 2,187,244 | Mills | Jan. 16, 1940 |
| 2,205,037 | Henke | June 18, 1940 |
| 2,316,670 | Colgate et al. | Apr. 13, 1943 |

FOREIGN PATENTS

| Number | Country | Date |
|---|---|---|
| 661,130 | Great Britain | Nov. 14, 1951 |